United States Patent [19]

Kawai et al.

[11] Patent Number: 4,457,863
[45] Date of Patent: Jul. 3, 1984

[54] ANTITUMOR SUBSTANCE

[75] Inventors: Kimitoshi Kawai; Kunio Sugawara; Tsuyoshi Morinaga, all of Ohimachi, Japan

[73] Assignees: Daicel Chemical Industries, Ltd., Osaka, Sapporo Breweries Ltd., Tokyo; Etsuo Ito, Okinawa, all of Japan.

[21] Appl. No.: 377,490

[22] Filed: May 12, 1982

Related U.S. Application Data

[63] Continuation of Ser. No. 177,161, Aug. 11, 1980, abandoned.

[30] Foreign Application Priority Data

Aug. 17, 1979 [JP] Japan .............................. 54-104683
Jun. 30, 1980 [JP] Japan .............................. 55-88756

[51] Int. Cl.$^3$ .............................................. C07G 7/00
[52] U.S. Cl. ................................ 260/112 R; 424/177; 424/195
[58] Field of Search .................... 260/112 R; 424/195

[56] References Cited

U.S. PATENT DOCUMENTS 2,271,620  2/1940  Bnir et al. ...................... 260/112 R

FOREIGN PATENT DOCUMENTS 1301002  9/1963  Fed. Rep. of Germany ...... 424/195
51-29212   3/1976  Japan ............................... 424/195
53-139713 12/1978  Japan ............................... 424/195

OTHER PUBLICATIONS

Huston et al., Cereal Chemistry, vol. 46, pp. 527-537 (1969).

Primary Examiner—John Kight, III
Assistant Examiner—Garnette D. Draper
Attorney, Agent, or Firm—Flynn, Thiel, Boutell & Tanis

[57] ABSTRACT

A new substance having antitumor activity is obtained from an epidermal portion of rice. A substance called RBF-P is obtained by adding ethanol to an aqueous alkaline extract of rice bran, removing the insolubles and precipitating the substance by addition of an acid. This substance comprises an active substance called RBF-PM, which is insoluble in methanol, and an active substance called RBF-X, which is soluble in acetone. The substance RBF-PM is a protein containing extremely little cystine and said protein can suppress solid cancers of mice. The substance RBF-X is a mixture of hexane-solubles such as fatty acids and a hexane-insoluble called RBF-H. A synergistic suppressive action on ascites hepatoma of mice is exhibited by the combination of the RBF-H and the fatty acids.

23 Claims, 6 Drawing Figures

ANTITUMOR SUBSTANCE

This is a continuation of application Ser. No. 177,161, filed Aug. 11, 1980, now abandoned.

BACKGROUND OF THE INVENTION

1. Field of the Invention

This invention relates to a new antitumor substance and, in particular, relates to a new substance having antitumor activity against certain types of tumors and containing protein, which substance is obtained from an epidermal portion of rice.

2. Description of the Prior Art

It is known from Japanese Patent Provisional Publication (hereinafter, referred to as JPPP) 50(1975)—77518, that a substance called RBA, having a physiological activity, is obtained by extracting rice bran with a solvent. The substance RBA is a phytalbumin containing 15–20 mole % of cysteine and 23–26 mole % of glycine, and it has an isoelectric point in the range of pH 7–pH 10. This RBA can be obtained, for example, by extracting rice bran with an aqueous sodium chloride solution.

It is also known from JPPP 53(1978)—139713 that an antitumor substance is obtained from an epidermal portion of a seed, such as grain, treated with heating under pressure. The thus-obtained substance, however, is a nonproteinaceous high molecular weight substance and is supposed to be a higher fatty acid or analog thereof, as described in the above-identified JPPP.

SUMMARY OF THE INVENTION

It is a primary object of the present invention to provide a new substance having an antitumor activity. "Antitumor activity" as used herein means activity against certain types of tumors, and is not meant to imply that the substance of the invention is necessarily effective against all tumors.

It is another object of the invention to provide a new process for the production of the substance having an anti-tumor activity from a raw material including an epidermal portion of rice.

It is a further object of the invention to provide a specific protein called RBF-PM containing only an extremely small amount of cystine.

It is a still further object of the invention to provide an antitumor drug containing, as the active ingredient, the substance RBF-PM.

It is a still further object of the invention to provide a composition having an antitumor activity.

Other objects of the invention will be apparent from the following contents of this specification.

These objects can be achieved by a substance which can be obtained by a series of steps comprising:
- extracting an epidermal portion of rice with an aqueous solution containing a base;
- mixing the aqueous extract solution with an organic solvent;
- removing the insolubles precipitated thereby; and
- adding an acid to the solution to precipitate the substance.

Further, these objects can be achieved by a second substance which is a component of the substance obtained in the above process. The second substance can be obtained from the first-mentioned substance by a solvent-dissolving process.

DESCRIPTION OF THE PREFERRED EMBODIMENTS

Figure 1:
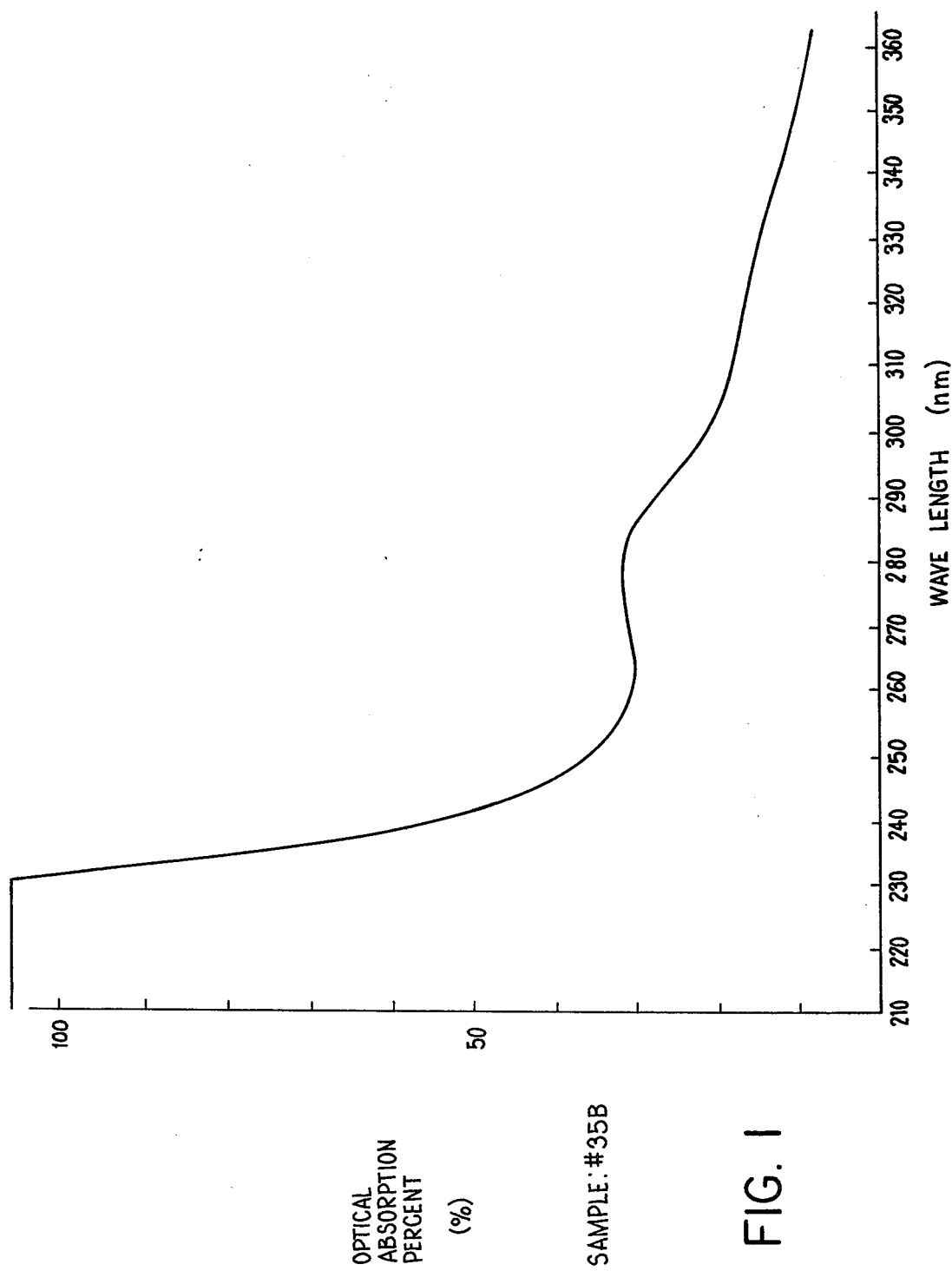
FIG. 1 shows a typical UV spectrum of a protein RBF-PM of the present invention.

As described hereinbefore, it is known from JPPP 53(1978)—139713 that an antitumor substance can be obtained from an epidermal portion of a seed, such as grain. According to the description in that publication, the starting material is heated under pressure, extracted with hot water or subjected to removal of a portion dissolved in hot water, and then extracted with an aqueous alkaline solution. The specification further describes in the example a more detailed description of the procedure: that is, the starting material, i.e., rice bran, is extracted with an aqueous alkaline solution; the thus-obtained solution is neutralized and concentrated; to the concentrated solution is added ethanol in an amount of 1.5 times as much as the amount of the solution; the precipitate produced upon the addition of ethanol is removed and then dissolved again in an aqueous alkaline solution; the insolubles are removed and the supernatant is purified by dialysis; and, thus, the desired substance is obtained as a white powder which is insoluble in acetone and methanol. The thus-obtained active substance is a nonprotein-type high molecular substance, and it is supposed to be a higher fatty acid or analog thereof.

The present inventors have studied the invention disclosed in the above-mentioned JPPP and have succeeded in obtaining an antitumor substance, hereinafter called RBF-P, containing a protein as a constituent substance, by treating the aqueous alkaline extract solution of rice bran in the manner different from that of the prior art. The substance RBF-P has, accordingly, properties different from those of the substance disclosed in the above-mentioned JPPP.

The thus-obtained substance RBF-P can be subjected to fractional extraction to give two active constituents, namely, a substance, hereinafter called RBF-PM, which is insoluble in methanol, and a substance, hereinafter called RBF-X, which is soluble in acetone. The former is a specific protein containing little cystine and it has an activity for suppressing solid cancers in mice. The latter is composed of hexane—soluble materials, such as fatty acids, and a hexane-insoluble substance, hereinafter called RBF-H. The combination of the RBF-H and the fatty acids can synergistically give a suppressive action on ascites hepatoma of mice.

The embodiments of the present invention are described hereinafter.

The new substance having an antitumor action called RBF-P can be obtained by mixing an aqueous alkaline extract, which has been obtained by extracting an epidermal portion of rice with an aqueous alkaline solution, with an organic solvent, removing the insolubles, and producing a precipitate by addition of an acid.

The epidermal portion of rice can be generally obtained in the form of rice bran which remains after recovering the cleaned rice from unpolished rice. However, rice with an intact epidermal portion, such as unpolished rice, per se, or residual rice bran remaining after removal of other useful ingredients, such as residual rice bran from which a rice bran oil has been extracted, can be likewise used as the starting material. Examples of rices include glutinous rice and nonglutinous rice, and species Japonica and species Indica. These species can be further divided into a variety of groups. There is no specific limitation on the kind and nature of the rice to be employed in the present invention. An example of a preferred and easily available raw material is rice bran produced from nonglutinous rice belonging to the species Japonica.

The rice bran contains an antitumor substance that is soluble in hot water, as disclosed in JPPP 53(1978)—139713. In contrast, the substance RBF-P of the present invention is obtained from the hot-water insoluble portion. Accordingly, the process for the production of the substance RBF-P is generally initiated by removal of the hot-water-soluble ingredients consisting essentially of polysaccharides such as starch, by treating the starting material with hot water. The process for the removal of the hot-water-soluble ingredients can be carried out by boiling rice bran with hot water in an amount of 5-20 times as much as the amount, by weight, of the rice bran. The heating process under pressure disclosed in JPPP 53(1978)—139713 can be likewise applied to the above-described first stage of the process of the present invention. The rice bran from which the hot-water soluble substances have been removed is then subjected, for instance, to extraction with an aqueous alkaline solution, such as an aqueous sodium hydroxide solution of 1-10 wt. % concentration. Other basic materials such as sodium carbonate, potassium hydroxide and ammonia can be likewise employed for that purpose in place of the sodium hydroxide. However, calcium hydroxide is not suitable, because it forms insoluble impurities during the extraction treatment. The amount of the base varies depending on the particular base employed. For instance, when sodium hydroxide is used, an amount thereof of 0.1 times as much as the amount, by weight, of the rice bran to be treated is sufficient.

The concentration of the aqueous basic (alkaline) solution, and the temperature and the time period of the extraction procedure have influences on the yield and activity of the substance RBF-P produced. If the extraction is carried out at 50° C. with 5% aqueous sodium hydroxide solution and the extraction period is about 5 hours, the yield of the produced substance RBF-P is high, but the activity is not satisfactory. Alternatively, if the extraction period is about 10 to 20 hours under the same extraction conditions, the substance RBF-P of excellent activity can be obtained. However, when the extraction period is about 30 hours under the same conditions, the yield and activity of the substance RBF-P produced are reduced seriously. Thus, in order to obtain the substance RBF-P of excellent activity, an appropriate extraction period should be selected, depending on the extraction temperature adopted. For instance, a longer period such as 100 hours, is adopted at an extraction temperature of 30° C. Temperatures lower than 10° C. and higher than 90° C. are not suitable for obtaining the substance RBF-P possessing satisfactory activity. As for the base concentration in the aqueous alkaline solution, a moderate concentration such as a concentration in the range of 1-10% is preferably selected.

In the prior art, an antitumor substance is obtained from the aqueous alkaline solution, that is, the aqueous alkaline extract of the epidermal portion of rice, by a series of steps, namely, neutralization, concentration, addition of ethanol, centrifuging, redissolution, readdition of ethanol, and finally dialysis for purification, as disclosed in JPPP 53(1978)—139713, Example 1.

In contrast to the above complicated process, the active substance RBF-P of the present invention, which is entirely different from the active substance of the JPPP 53(1978)—139713, can be obtained by remarkably simple steps, that is, mixing of the aqueous alkaline extract with an organic solvent, removal of the insolubles thereby produced, and precipitation by addition of an acid.

The process of the present invention is now described hereinafter in more detail.

The aqueous alkaline extract of rice bran, or like epidermal portion of rice, is mixed with an organic solvent miscible with water, such as ethanol, methanol or acetone, thereby precipitating insolubles in the solution. The thus-obtained insolubles are undesired ingredients, and they can be substantially completely precipitated, for instance, by the addition of ethanol so that the ethanol concentration in the mixture can exceed 40% by volume. The insolubles thus precipitated can be removed by centrifuging or filtration.

There is no specific limitation on the organic solvent that is to be mixed with the aqueous alkaline extract, provided that it is miscible with water. However, an organic solvent having an acidic nature is not appropriate, because it combines with the base in the alkaline extract. Ethanol or acetone, which are generally employed in the fractionation of a protein, is preferably employed. In addition to those solvents, lower alcohols such as methanol, n-propanol or isopropanol, polyvalent alcohols such as ethylene glycol, propylene glycol or glycerol, and glycol ethers such as ethoxyethanol or butoxyethanol can be generally employed. Moreover, ethers and ketones such as dioxane, tetrahydrofuran and methyl ethyl ketone, can be employed, provided that they are miscible with water. As described above, the generally employed organic solvents contain an oxygen atom in their molecular structure. However, other water-miscible solvents such as acetonitrile, dimethylformamide and pyridine, can be likewise employed in certain cases.

The amount of the organic solvent employed for the above-identified purpose, depending on the kind of a solvent used, is preferably in the range of 1/5 or larger times by volume, based on the volume of the aqueous alkaline solution. If ethanol is employed as the solvent and the ethanol concentration after being mixed with the aqueous alkaline solution is adjusted to reach 40% by volume, the undesired polysaccharides extracted together with the desired substance, in the aqueous alkaline solution, are precipitated. Thus, the polysaccharides can be removed. If the ethanol concentration, however, exceeds 60% by volume, the precipitation of the substance RBF-P upon addition of an acid in the following step is prevented. It gives a good result to use methanol in an amount as large as 4 to 5 times.

Accordingly a preferable amount of an organic solvent is 1/5 to 5 times by volume, based on the volume of the aqueous alkaline solution.

In this specification, the term "percent" is generally used to mean "percent by weight." But the term "percent" is based on volume in the above description of the organic solvent concentration.

The aqueous alkaline extract is thus treated to remove the undesired substances, and subsequently neutralized with an acid, such as hydrochloric acid, phosphoric acid or acetic acid, to produce a precipitate, that is, the substance called RBF-P. The thus-produced precipitate is subsequently dried by heating under reduced pressure, freeze-drying of spray-drying to obtain a dry substance.

The precipitating procedure for obtaining the precipitate by the neutralization of the aqueous organic solution is usually done only once. However, if additional purification is required, another precipitating procedure, similar to the first one, can be further carried out. If the double purification is to be done, the first purification procedure is preferably carried out under conditions in which the ethanol concentration is adjusted to a lower value ranging from 10 to 40% by volume, for instance, 30% by volume, and the neutralization is done to an end point ranging from pH 5 to 6, whereby the loss of the active substance can be reduced. Subsequently, the second purification procedure is carried out by redissolving the thus-obtained precipitate in an aqueous alkaline solution, adding ethanol in an amount so that the ethanol concentration in the aqueous solution can reach a higher value such as 50% by volume, removing the thus-produced insolubles, and adjusting the pH level of the solution by addition of an acid to produce the precipitate. When the pH level at the end point is 7, only 22 wt. % of the solid portion in the solution is precipitated. However, an end point pH level of 6 precipitates 74 wt. % of the solid portion; and further, pH 5 gives 74 wt. %, pH 4 gives 59 wt. % and pH 3 gives 36 wt. %. Thus, the solid portion behaves differently from a fatty acid that precipitates automatically in an acidic condition. In contrast, the present solid portion can precipitate only in an appropriate pH range in the same manner as a protein that precipitates only at its isoelectric point. As is obvious from the above description, the neutralization in the procedure of the present invention is preferably carried out to an end point in a range of pH 3–7, and, more preferably, a level in the range of pH 4–6 can be adopted.

The substance RBF-P thus obtained is effective for suppressing ascites tumor and solid tumor in mice. Moreover, the substance RBF-P can be effectively employed together with other antitumor drugs, such as Mitomycin-C. The antitumor action of the substance RBF-P is considered to stem from the two ingredients described hereinbelow.

The protein RBF-PM according to the present invention is one of the antitumor ingredients of the substance RBF-P and is newly obtained by the present invention. The protein RBF-PM has little cystine. It is obtained as a methanol-insoluble fraction of the substance RBF-P. The substance RBF-PM can be produced, for instance, by the following steps: one liter of methanol is added to 10 g. of the substance RBF-P; the methanol-soluble substance is then dissolved in the methanol under stirring; the insoluble substance is removed by filtration and then the methanol-insoluble substance is dried to give about 3 g. of the substance RBF-PM.

The thus-obtained protein RBF-PM has the characteristics described below:

Protein coloring reaction (Lowry method): more than 90% as bovine serum albumin; e.g., 93% for the product #20 set forth in the following Table 1

Saccharide coloring reaction (phenol-sulfuric acid method): less than 8%, as glucose UV spectrum: weak absorption in the vicinity of 280 $\mu$m, as seen in FIG. 1

Figure 2:
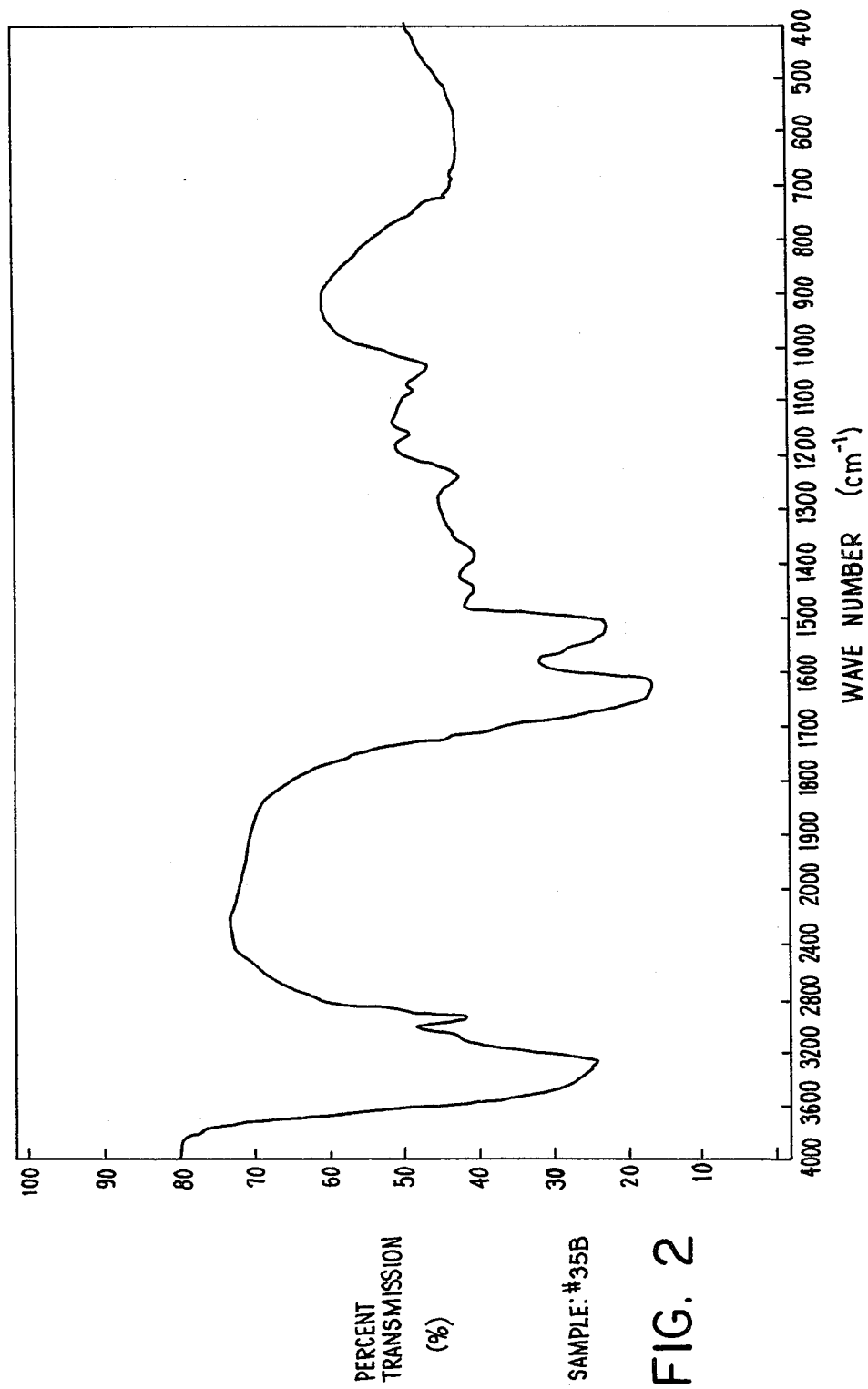
FIG. 2 shows a typical IR spectrum of the protein RBF-PM of the invention.

IR spectrum: prominent absorptions in the vicinities of 3300, 1640 and 1530 cm$^{-1}$, as seen in FIG. 2

Melting point: no critical melting point observed up to 300° C.

Elementary analysis: Some examples are set forth in the following Table 1. It is noted that the nitrogen content is relatively low; i.e., in the range of 12–15 wt. %, particularly 12–14 wt. %.

Isoelectric point: No relocation of the spot takes place in the standard type isoelectric electrophoretic analysis. The minimum UV absorption of the solution is observed at pH 3–6; e.g., 3.5–5 for the product #20 set forth in the following Table 1.

Amino acid analysis: as described below:

Procedure of amino acid analysis

The protein is hydrolyzed at 110° C. for 24 hours with 6N hydrochloric acid, and then the hydrochloric acid is evaporated. To the residue is added 0.01N aqueous sodium hydroxide solution, and this mixture is is allowed to stand at room temperature for 4 hours. Subsequently, this mixture is acidified with 0.1N hydrochloric acid, and analyzed by the ion exchange chromatography and the ninhydrin coloring method.

If cysteine is included in the protein, the cysteine is observed as cystine because the cysteine is converted to cystine in the course of the alkaline treatment. The term "cystine content" used in the specification and claims is intended to include any cysteine that was originally present in the protein in the form of cysteine.

Exemplary analytical data of the amino acid compositions of the proteins included in the present invention are set forth in Table 1, as well as the standard amino acid compositions of the protein.

TABLE 1

| | | (unit: % by weight) | | | |
|---|---|---|---|---|---|
| | RBF-PM | Product No. | | | |
| Amino acid | (range) | #20 | #35B | #37 | #46 |
| Aspartic acid | 8–12 | 9.5 | 9.2 | 9.0 | 10.1 |
| Threonine | 1–5 | 4.3 | 3.0 | 2.9 | 2.9 |
| Serine | 1–5 | 4.6 | 2.5 | 2.8 | 2.6 |
| Glutamic acid | 11–16 | 14.6 | 13.2 | 13.6 | 14.7 |
| Proline | 1–5 | 1.6 | 4.0 | 3.4 | 3.2 |
| Glycine | 4–8 | 5.5 | 5.9 | 6.2 | 6.4 |
| Alanine | 5–9 | 6.8 | 6.9 | 7.1 | 7.0 |

TABLE 1-continued

| | | | | | |
|---|---|---|---|---|---|
| Cystine | less than 0.1 | un-detected | undetected | undetected | undetected |
| Valine | 7–12 | 8.0 | 10.4 | 9.4 | 9.6 |
| Methionine | 1–3 | 2.3 | 1.1 | 1.5 | 1.3 |
| Leucine | 8–16 | 8.7 | 14.4 | 14.0 | 13.6 |
| Isoleucine | 4–8 | 7.6 | 5.7 | 5.2 | 5.0 |
| Tyrosine | 2–5 | 4.6 | 3.3 | 3.5 | 3.3 |
| Phenyl-alanine | 5–9 | 6.5 | 6.7 | 7.1 | 7.0 |
| Lysine | 3–6 | 4.7 | 4.8 | 4.9 | 4.8 |
| Histidine | 1–5 | 2.8 | 2.8 | 3.3 | 2.9 |
| Arginine | 4–9 | 7.9 | 6.3 | 6.3 | 5.9 |
| Elementary analysis | RBF-PM (range) | #20 | #35B | #37 | #46 |
| C | 47–54 | 48.89 | 51.19 | 51.22 | 52.01 |
| H | 6–8 | 6.91 | 7.04 | 7.10 | 6.97 |
| N | 12–15 | 13.56 | 12.31 | 13.54 | 13.97 |
| Amount of saccharide (phenol-sulfuric acid method) | 0–8 | 0.9–1.1 | 4.5–6.9 | 3.5–5.5 | 0.6–1.8 |

Liquid chromatography

Figure 3:
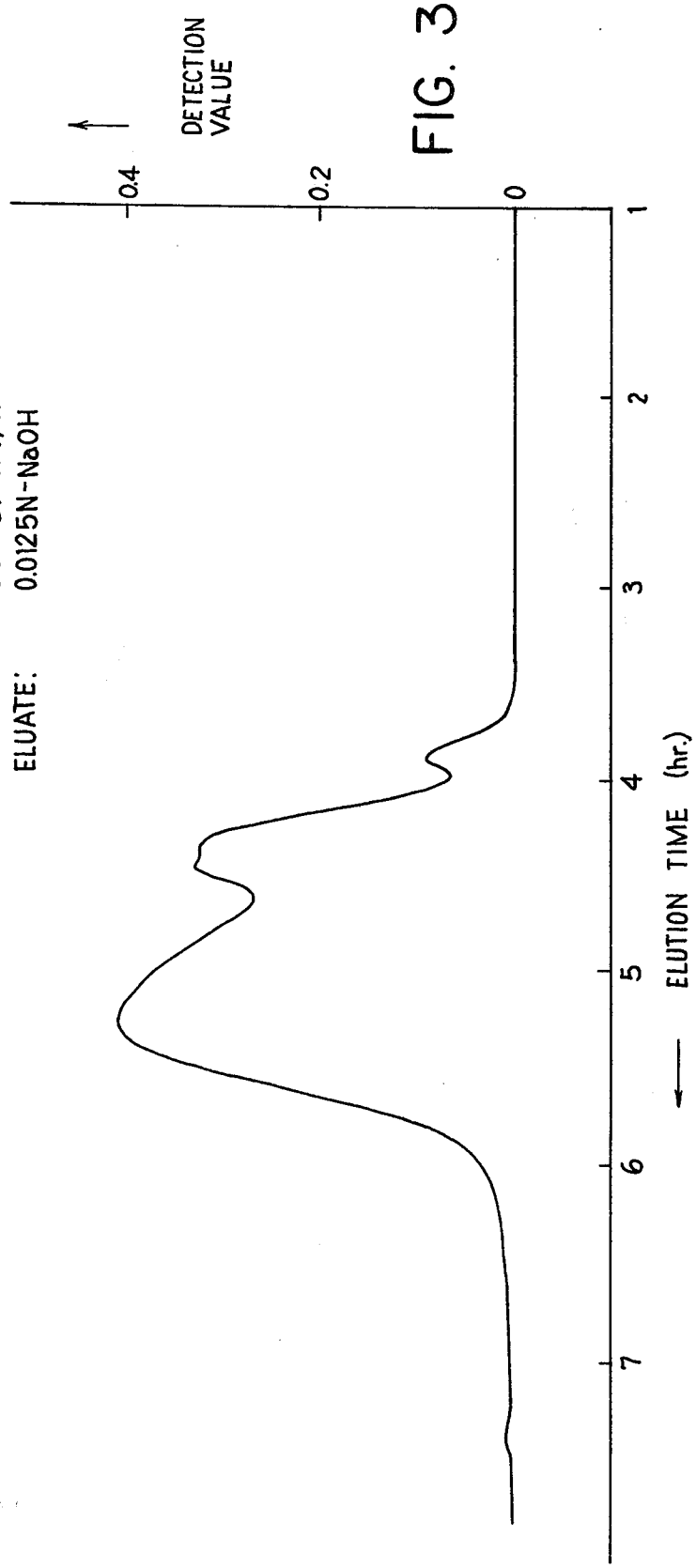
FIG. 3 shows a typical liquid chromatographic analysis result, using Toyopearl 60, of the protein RBF-PM of the invention.

An exemplary elution chromatography analysis result is illustrated in FIG. 3. Resin material charged into the column: Toyopearl (registered trademark of Toyo Soda Mfg. Co., Ltd, Japan)HW60 (porous gel particles prepared by polymerization of a hydrophilic vinyl monomer) Eluent: 0.0125N aqueous sodium hydroxide solution.

Comparison with the elution time of a control sample indicates that the molecular weight of the substance RBF-PM is mainly distributed in both of the ranges 30,000–50,000 and 70,000–120,000.

Solubility

Procedure for evaluation: 1 mg. of the sample to be tested and 1 ml. of the solvent to be tested are mixed at room temperature, and the observation is made with the naked eye.

Solvents in which RBF-PM is insoluble or sparingly soluble

Pure water, 0.85% aqueous sodium chloride solution, methanol, ethanol (100%, 70%), acetone, methyl ethyl ketone, ethyl ether, isopropyl ether, ethyl acetate, butyl acetate, 7-M aqueous urea solution, phosphoric acid buffer (pH 4.7–7), citric acid buffer (pH 3.3–7), acetic acid buffer (pH 3.7–8.1), hydrochloric acid (0.1N, 6N), and 0.1-M aqueous acetic acid.

Solvents in which RBF-PM is partly soluble 3M guanidine hydrochloride solution (aqueous solution).

Solvents in which RBF-PM is completely soluble 6M guanidine hydrochloride solution (aqueous solution), aqueous sodium hydroxide solution (0.0125N), aqueous alkaline alcoholic solution (0.0125N, 50% in volume), aqueous sodium laurylsulfate solution (0.1%), aqueous sodium dodecylbenzenesulfonate solution (0.1%) and glacial acetic acid.

There have been a great number of disclosures with respect to the amino acid compositions constituting proteins and, for instance, there are disclosed tables of analytical data of amino acid compositions constituting a great number of proteins and foods in Protein Chemistry (in the Japanese language), edited by Mizushima and Akabori, Kyoritsu Shuppan Co., Ltd., 1954, Vol. 2, pp. 127–149. As is well known, cystine serves an important role in proteins to constitute the three dimensional structure. Therefore, most proteins contain not less than approximately 1% of cystine in the molecule, as is seen from the tables identified above. Even the tables teach a small number of exceptional proteins containing no cystine, but most of these proteins contain a higher amount of nitrogen. Thus, there can be seen no proteins containing 12–15% of nitrogen and less than 0.1% of cystine in the aforementioned tables. Accordingly, the proteinaceous substance RBF-PM of the present invention is characterized by an exceptional chemical composition, and further, by the solubility and the specific isoelectric point in the range of pH 3–6, inclusive.

The proteins of rice can be classified into 4 protein groups, i.e., albumin, globulin, glutelin and prolamin, according to a classification based on the solubility of the protein. They are generally contained in a red rice bran in the amounts of, for instance, 3.87 wt. %, 3.74 wt. %, 0.58 wt. % and 2.39 wt. %, respectively, according to the description on the proteins in rices included in Horikoshi & Morita, Experimental Procedures for Studying Plant Enzymic proteins, page 451, Kyoritsu Shuppan Co., Ltd., Japan (1976).

Albumin is soluble in pure water and globulin is insoluble in pure water. However, both are soluble in a dilute aqueous salt solution. In contrast, prolamin and glutelin are both insoluble in a dilute aqueous salt solution, but are soluble in dilute acid or alkali solution. Both are insoluble in pure alcohols, but prolamin is soluble in 60–90% alcohol. Both of glutelin and prolamin contain a relatively large amount of glutamic acid and proline, and prolamin is particularly rich with proline.

Examples of the amino acid compositions of glutelin contained in rice are described in the aforementioned reference of Horikoshi & Morita. According to the reference, glutamic acid is particularly high, followed by aspartic acid and alginine, and cystine is contained in the amount of 1–2%.

There is also known the amino acid composition of the standard protein sample of rice bran that is obtained by extracting defatted rice bran with an aqueous alkaline solution, and producing a precipitate by addition of an acid (Mitsuda et al., "Nutrition and Food," Vol. 32, 82). According to this reference, a predominant amino acid is glutamic acid, and the cystine content is approximately 2%.

The protein RBF-PM, according to the present invention, is insoluble in all of pure water, a dilute aqueous salt solution and alcohol (100% and 70%), but it is soluble in a dilute aqueous alkaline solution. Therefore, the protein RBF-PM is similar to glutelin from the viewpoint of the solubility, but it is different therefrom because the former is insoluble in a dilute aqueous acid. A particularly characteristic aspect of the protein RBF-PM resides in that the cystine content is extremely low. It is also noted that it contains a small amount of a saccharide.

The substance RBF-PM is, moreover, related to the substance RBA disclosed in JPPP 50(1975)—77518, with respect to the facts that both substances are proteins having physiological activity and both are obtained from rice bran. However, the substance RBA is obtained by extraction with a solvent, such as an aqueous sodium chloride solution, and it has a higher cystine content such as a value of 15-20%. In contrast to these characteristics, the substance RBF-PM, according to the present invention, is insoluble in an aqueous sodium chloride solution and it has an extremely low cystine content. It is noted that the analytical method employed and cited herein quantitatively includes the cysteine content as part of the cystine content.

The protein RBF-PM of the present invention is of value as a physiologically active substance. Particularly, this protein has a prominent antitumor activity, and its suppressive effects on the metastasis of tumors in mice are remarkable, as shown in the examples hereinafter given.

The second ingredient that contributes for providing the antitumor activity of the substance RBF-P, namely RBF-X, can be obtained by treating the substance RBF-P with a polar organic solvent and collecting the soluble portion.

Examples of the polar organic solvents include alcohols, such as methanol, ethanol, n-propanol, isopropanol and butanol, ketones such as acetone, methyl ethyl ketone and cyclohexanone, and ethers, such as isopropyl ether and tetrahydrofuran. The polar organic solvent is generally recovered by evaporation after removal of the soluble portion through the extraction. Accordingly, the polar organic solvent preferably has the boiling point of not higher than 150° C. A combination of these polar organic solvents can be employed. Certain aqueous polar organic solvents can also provide desired results in the yield of the active substance and the antitumor activity. In view of the mode of use of the solvent, an aqueous acetone solution containing not less than 70 wt. % of acetone and an aqueous ethanol solution containing not less than 60 wt. % of ethanol are preferably employed, because they show satisfactory compatibility and volatility.

The substance RBF-P is treated with the polar organic solvent so that it is dissolved, leaving a certain insoluble portion. Thus, a solution containing the substance RBF-X, the portion soluble in the polar organic solvent, is obtained. The insoluble portion essentially corresponds to the aforementioned substance RBF-PM. However, if the polar organic solvent employed is diethyl ether or the like a small amount of the fatty acid salt that has been contained in the starting substance RBF-P sometimes remains in the insoluble portion. The fatty acid salt can be dissolved in methanol.

The antitumor substance RBF-X that can be recovered by removal of the solvent through evaporation of the solution consists of a hexane-insoluble portion and a hexane-soluble portion. The principal ingredient of the hexane-soluble portion is a known higher fatty acid such as palmitic acid, oleic acid or linoleic acid. It is known that a higher fatty acid, particularly an unsaturated higher fatty acid, has an antitumor activity. However, since the antitumor activity of fatty acids contained in fats and oils generally is weak, they are not yet employed practically as antitumor drugs for therapeutic treatment. In view of these facts, the antitumor activity of the substance of the present invention cannot be based on only the amount of the fatty acid contained as the hexane-soluble fraction in the substance.

The hexane-insoluble substance is a powder varying in color from white to pale brown, and the precise chemical structure thereof is not known. Therefore, this substance is named RBF-H for identificaton purposes. The characteristic properties of the substance RBF-H are as follows:

Phenol-sulfuric acid reaction (coloring reaction for saccharide): —

Protein coloring reaction (Lowry method): ++

Biuret reaction (coloring reaction for protein): ++

Figure 4:
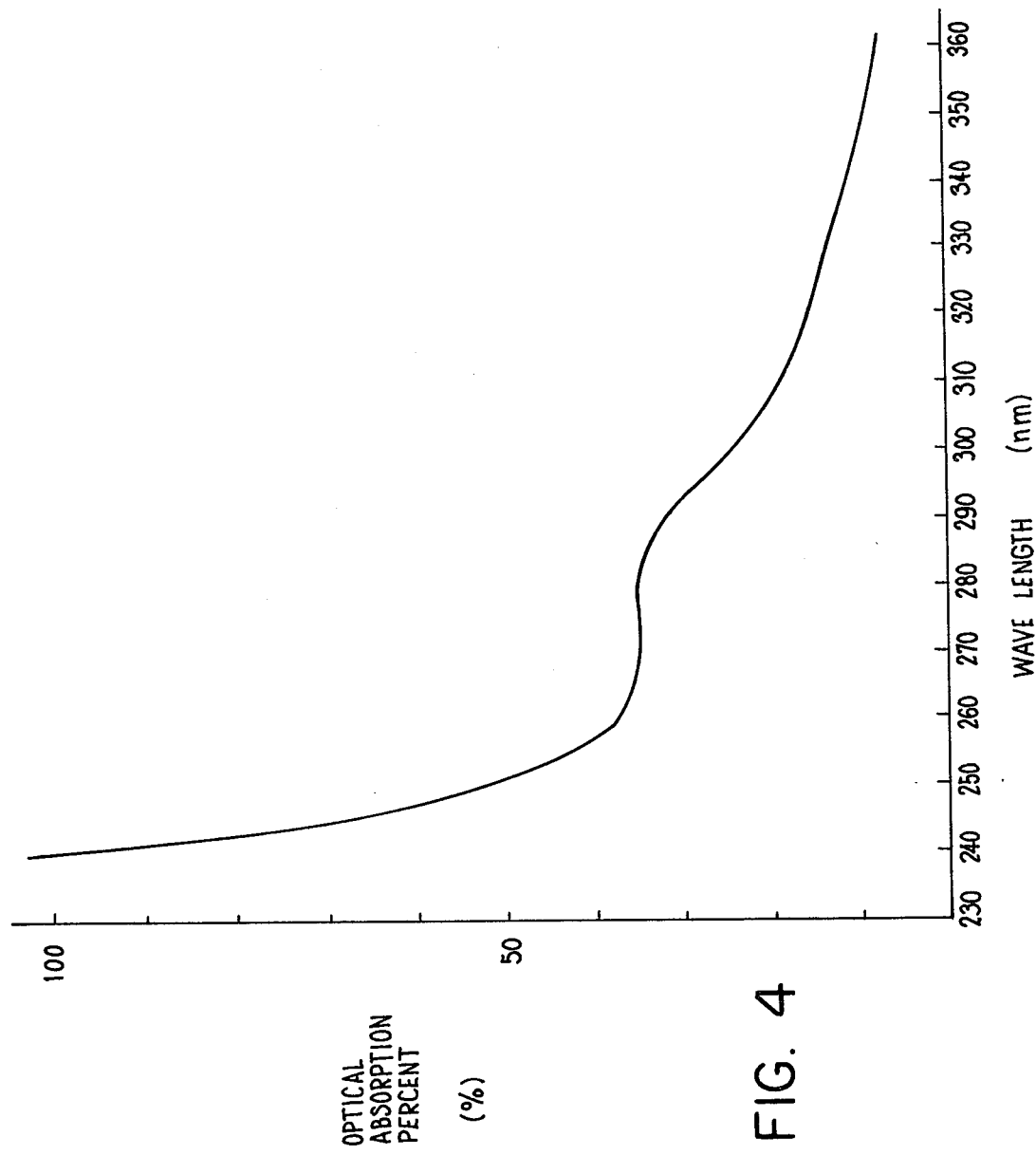
FIG. 4 shows a typical UV spectrum of a substance RBF-H of the present invention.

UV spectrum: weak absorption in the vicinity of 280 $\mu$m, as seen from FIG. 4

Figure 5:
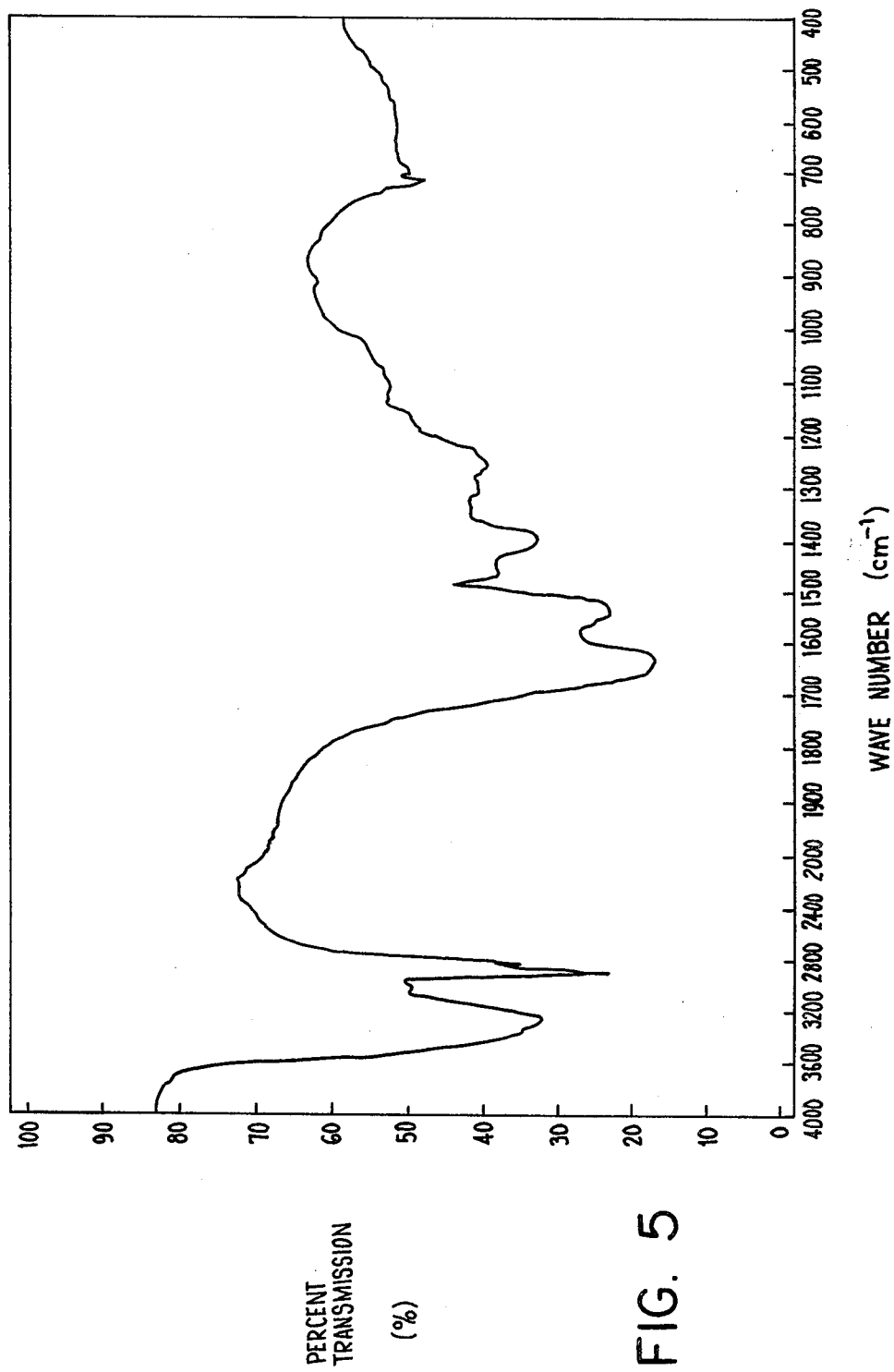
FIG. 5 shows a typical IR spectrum of the substance RBF-H of the invention.

IR spectrum: prominent absorptions in the vicinities of 3300, 2900, 1640 and 1530 cm$^{-1}$, as seen from FIG. 5

Elementary analysis: C, 52.43%; H, 7.79%; N, 6.67%; Ash, 4.36%. The examinations of antitumor activity of the substance RBF-H revealed that this substance is effective per se against solid tumors. However, it was found that the use of the substance RBF-H, by itself, shows no action in assay on antitumor activity based on TPCV (Total Packed Cell Volume) method using the ascites type sarcoma 180. Nevertheless, the substance RBF-H surprisingly shows a powerful antitumor activity when it is employed in conjunction with a fatty acid. As described hereinbefore, the second ingredient substance RBF-X, which is capable of contributing the antitumor activity of the substance RBF-P, contains a higher fatty acid as the hexane-soluble fraction. Consequently, it is assumed that said substance RBF-X forms together with the substance RBF-H, that is inactive per se against ascites tumor, a composition having the powerful antitumor activity, thereby showing a prominent synergistic action.

Accordingly, the present invention, in one aspect thereof, is concerned with the new antitumor substance RBF-P that can be obtained by extracting an epidermal portion of rice with an aqueous solution containing a base; mixing the aqueous extract solution with, for instance, ethanol to reach an ethanol concentration of 50 vol. %, so that the undesired materials can be removed; adding an acid to the solution to, for instance, pH 5, so that the desired substance can be precipitated. The thus-obtained substance RBF-P contains both active ingredients, i.e., the specific protein RBF-PM and a polar organic solvent-soluble substance RBF-X. The present invention, accordingly, employs the same starting material as does the prior art cited hereinbefore. But the procedures for the respective separations are entirely different from one another. It is pointed out that the desired substance of the present invention can be produced on an industrial scale, without employing industrially troublesome purification processes, i.e., dialysis of an alkaline solution.

From the viewpoint of chemical nature, the substance RBF-PM is a protein, and the substance RBF-H contained in the acetone-soluble portion RBF-X is also a proteinaceous substance. In this respect, the substances of the present invention are apparently different from the substance disclosed in the cited publication (JPPP 53(1978)-139713) whose action is described to be caused by the nonproteinaceous high molecular substance contained therein and which is insoluble in acetone and methanol.

In conclusion, the present invention provides a previously unknown antitumor substance obtained from rice bran or the like.

The present invention is further described by reference to the following illustrative examples, but these examples are not to be construed to restrict the invention.

EXAMPLE 1

To 16 kg. of rice bran obtained from a mixture of rice grains belonging to species of Shonai sasanishiki, Iwate kiyonishiki and Saitama nihonbare was added 216 l. of water, and the mixture was heated under pressure at 120° C. for 1 hour. Subsequently, the mixture was kept at 100° C. for 4.5 hours to dissolve the portion soluble in hot water. The resulting mixture was filtered while hot to collect 22.4 kg. of the solid portion. To the whole of the solid portion was added 40 kg. of 5% aqueous sodium hydroxide solution, and the mixture was stirred at 50° C. for 10 hours, for the purpose of extraction. To 60.3 kg. of the extract was then added 60.3 l. of water, and subsequently 120.6 l. of ethanol was added to the aqueous extract, so that the ethanol concentration reached 50% by volume.

The alkaline ethanol-insoluble fraction was removed by centrifuging, and the solution was adjusted to pH 5.5 by addition of hydrochloric acid. The thus-produced acidic solution was allowed to stand overnight at a temperature of lower than 10° C. and the precipitate was collected. The precipitate was then dried by a freeze-drying procedure to give 1.46 kg. of the freeze-dried product RBF-P.

To 10 g. of the thus-obtained product RBF-P was added 1 l. of methanol, and the methanol-soluble portion was removed. Thus, there was obtained 3.2 g. of the protein RBF-PM as the methanol-insoluble fraction (this is substance #35B described in Table 1).

The same procedure as described above was repeated to obtain 1.54 kg. of the substance RBF-P. This was then treated with methanol to give a methanol-insoluble substance RBF-PM in the yield of 32.5% based on the amount of the substance RBF-P. This methanol-insoluble substance is the substance #37 in Table 1.

The same procedure as described above was repeated except tat the rice bran was obtained from a mixture of rice grains belonging to the species of Fukushima sasanishiki and Saitama nihonbare. There was obtained 1.30 kg. of the substance RBF-P, from which the substance RBF-PM was obtained in the yield of 30.7% based on the amount of the substance RBF-P. This methanol-insoluble substance is substance #46 in Table 1.

EXAMPLE 2

Cells of ascites type sarcoma 180 cultivated in the peritoneal cavity of ICR mice for 7 days were transplanted, in numbers of $5.6 \times 10^6$ cells per mouse, into the peritoneal cavity of ICR mice, female, 5 weeks age. Seven mice were included in each test group. After 24 hours had passed, an aqueous saline solution containing the sample to be tested was administered into the peritoneal cavity of the mice of one test group once a day, for 5 days. The amount of the tumor cells cultivated in the abdomen was determined by measuring the sedimentation volume on the 7th day after the cell transplantation. The same procedures for the measurement were carried out on the control group. The tumor-inhibiting ratio was calculated according to the equation described below.

$$\text{Inhibiting Ratio (\%)} = \left(1 - \frac{\text{Tumor Volume (Sample)}}{\text{Tumor Volume (Control)}}\right) \times 100$$

The protein RBF-PM #35B obtained in Example 1 showed an inhibiting ratio of 62%, when administered at a dosage of 100 mg./kg. day.

EXAMPLE 3

Cells of ascites type sarcoma 180 cultivated in the peritoneal cavity of ICR mice for 7 days were transplanted, in numbers of $3 \times 10^6$ cells per mouse, into the muscles of the right hind legs of ICR mice, female, 5 weeks age. Five to seven mice were included in each test group. After 24 hours had passed, an aqueous saline solution containing the sample to be tested was administered into the peritoneal cavity to the mice of one test group, once a day for 10 days. The tumors in the mice were taken out on the 28th day after the cell transplantation and weighed for comparing with the results obtained by the control sample. The tumor-inhibiting ratio was calculated according to the equation described below.

$$\text{Inhibiting Ratio (\%)} = \left(1 - \frac{\text{Tumor Weight (Sample)}}{\text{Tumor Weight (Control)}}\right) \times 100$$

The result obtained by the use of the protein RBF-PM (#35B) is shown below:

| Dosage (mg./kg. · day) | Route of Administration | Inhibiting Ratio (%) |
|---|---|---|
| 1 | Intraperitoneally | 45 |

EXAMPLE 4

To 4 kg. of rice bran obtained from rice grains belonging to species koshihikari was added 16 l. of water, and the mixture was heated under pressure at 120° C. for 1 hour. Subsequently, the mixture was kept at 100° C. for 4.5 hours to dissolve the portion soluble in hot water. The resulting mixture was filtered while hot to collect the solid portion. The thus-obtained solid portion was mixed with 10 kg. of 4% aqueous sodium hydroxide solution, and the resulting mixture was allowed to stand at 20° C. for 48 hours to extract a portion soluble in an aqueous basic solution. To the extract was added 5 l. of water, and the aqueous mixture was filtered. To the filtrate was added 6.3 l. of ethanol so that the ethanol concentration was adjusted to 30% by volume. After the addition, the solution was neutralized with hydrochloric acid to reach pH 5, and then allowed to stand at 4° C. for 24 hours. The precipitate thus produced was collected by centrifuging and washed twice with water to obtain 1.3 kg. of a wet cake. The wet cake was dissolved in 3.5 kg. of 1% aqueous sodium hydroxide solution, and 4.8 l. of ethanol was added to this solution so that the ethanol concentration reached approximately 50% by volume. The alkaline ethanol-insoluble was produced, and this was removed by filtration. The filtrate was neutralized to pH 5.5, and allowed to stand overnight. The precipitate thus produced was collected by filtration and dried to give 122 g. of the substance RBF-P in the form of a dry precipitate. This yield corresponded to 74% yield based on 165 g. of the dialysis membrane-impermeable solid portion that had been contained in the filtrate in advance of the neutralization.

Figure 6:
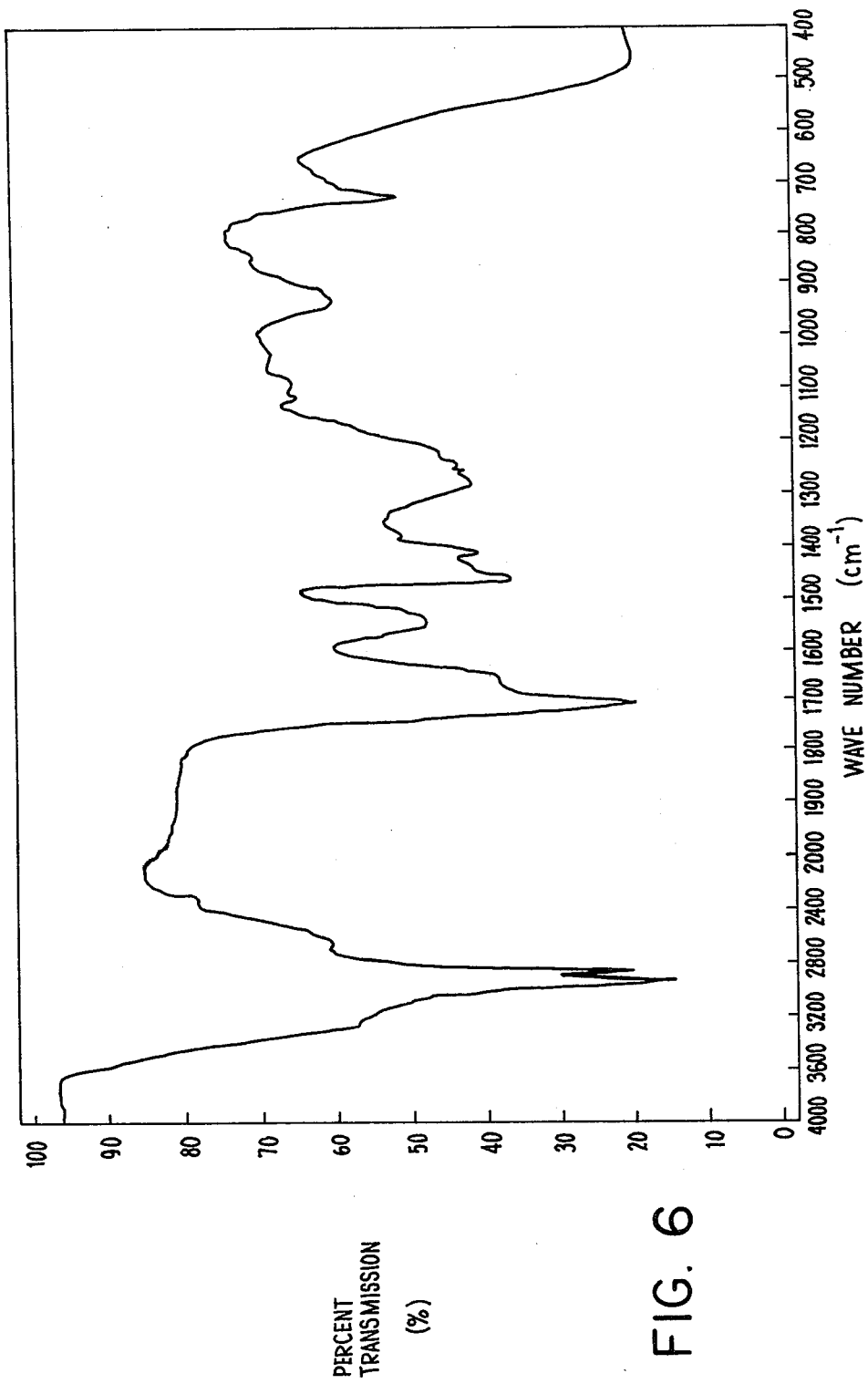
FIG. 6 shows a typical IR spectrum of a substance RBF-X of the present invention.

To 10 g. of the substance RBF-P obtained in the above was added 350 ml. of 80% acetone (the aqueous acetone concentration is expressed in volume ratio, and this is the same hereinafter) to extract the 80% acetone-soluble portion from the substance RBF-P. The solvent was then removed by evaporation to leave 8.1 g. of the 80% acetone-soluble portion. The IR spectrum of the thus-obtained portion is shown in FIG. 6. To this portion was added 35 ml of n-hexane, so that the soluble portion was removed. The n-hexane insoluble portion, i.e., the substance RBF-H, amounted to 1.13 g. The UV and IR spectra of RBF-H are shown in FIGS. 4 and 5, respectively. The n-hexane-soluble portion comprised 12% of palmitic acid, 38% of oleic acid and 34% of linoleic acid. Thus, the principal ingredient was higher fatty acids.

To 10 g. of the aforementioned substance RBF-P was added 1 l. of methanol, and the methanol-soluble portion was thus removed. There was obtained 3.7 g of the substance as the methanol-insoluble fraction. This is the substance #20 set forth in Table 1.

The inhibiting effect against solid tumors in mice was examined in the same manner as described in Example 3. The results are as follows for substance #20:

| Dosage (mg./kg. · day) | Route of Administration | Inhibiting Ratio (%) |
| --- | --- | --- |
| 1 | Intraperitoneally | 80 |
| 1 | Orally | 32 |
| 10 | Orally | 41 |

Example 5

(Test for Antitumor Activity)

Cells of ascites type sarcoma 180 cultivated in the peritoneal cavity of ICR mice for 7 days were transplanted, in numbers of $5 \times 10^6$ cells per mouse, into the peritoneal cavity of ICR mice, female, 5 weeks age. Five mice were included in each test group. After 24 hours had passed, an aqueous saline solution containing the sample to be tested was administered into the peritoneal cavity once a day, for 5 days. The amount of the tumor cells cultivated in the peritoneal cavity was determined by measuring the sedimentation volume on the 7th day after the cell transplantation. The same procedures for the measurement were carried out on the control sample, and the tumor-inhibiting ratio was calculated according to the equation described below.

$$\text{Inhibiting Ratio (\%)} = \left(1 - \frac{\text{Tumor Volume (Sample)}}{\text{Tumor Volume (Control)}}\right) \times 100$$

The inhibiting ratios of the substance RBF-P obtained in Example 4 were 81% for a dosage of 100 mg./kg.·day (the unit of the dosage is the same hereinbelow) and 42% for the dosage of 50. The inhibiting ratios of the 80% acetone-soluble portion taken out of the corresponding substance RBF-P were 100% even for the dosage of 50. The substance RBF-H obtained by removal of the n-hexane soluble portion showed no inhibiting effect even when the dosage was 100.

EXAMPLE 6

The substance RBF-P obtained in Example 4 was treated with a variety of polar organic solvents to separate the soluble portion RBF-X. The yield of the soluble portion and the antitumor activity were determined. The results are shown in Table 2.

TABLE 2

| Solvent | 70% Acetone | 90% Acetone | 100% Acetone | Ethyl Acetate | Ether Ethyl | 80% Ethanol | 60% Ethanol |
| --- | --- | --- | --- | --- | --- | --- | --- |
| Yield (%) | 83 | 70 | 68 | 68 | 65 | 85 | 79 |
| Inhibiting Ratio (%) (Dosage) | 100 (50) | 100 (50) | 98(100) 61(50) | 85(100) — | 98(100) 71(50) | 64(50) — | 100 (50) |

EXAMPLE 7

In the step for precipitating the substance RBF-P by neutralizing the 50% ethanol solution described in Example 4, different pH levels were employed to produce the precipitates, and the antitumor activities of the precipitates were determined. The precipitate produced at pH 6 yielded 74%, and showed an inhibiting ratio of 96% for the dosage of 100. Accordingly, this condition gave satisfactory results, like the condition described in Example 4. The precipitate produced at pH 3 decreased to yield 36%, and the inhibiting ratio was 84% for the dosage 100. However, no inhibiting action was observed in the dosage of 50. The precipitate produced at pH 7 further decreased to yield 22%, and no inhibiting action was observed with the thus-obtained precipitate. The mother liquor obtained in the procedure employing the pH 7 level was then made to pH 5, to produce a precipitate. This precipitate showed the inhibiting ratio of 64% for the dosage 50.

From all of the active precipitates obtained as described above, the soluble portion RBF-X was obtained in a yield ranging from 60 to 80%, based on the starting material RBF-P, by extraction with 80% acetone. The 80% acetone-insoluble portion RBF-PM obtained in the above procedure amounted to 20-40% based on the starting material RBF-P.

EXAMPLE 8

The substance RBF-H and higher fatty acids obtained in Example 1 were examined, singly or in combination, with respect to their antitumor activity. The results are set forth in Table 3. As is seen from the results in Table 3, the substance RBF-H and the higher fatty acids, neither of which showed a remarkable inhibiting action when employed singly in the dosage adopted, showed a remarkably higher inhibiting ratio not less than 90% when employed in combination.

TABLE 3

|  | Experiment No. | 1 | 2 | 3 | 4 | 5 | 6 | 7 | 8 | 9 | Reference Compound |
|---|---|---|---|---|---|---|---|---|---|---|---|
| Dosage (mg/kg · day) | Palmitic acid | 5 |  |  |  | 5 | 5 |  |  | 5 | 5-Fluorouracil (3 mg./kg. · day) |
|  | Oleic acid |  | 17 |  |  | 17 | 17 | 17 | 17 |  |  |
|  | Linoleic acid |  |  | 14 |  | 14 | 14 | 14 | 14 |  |  |
|  | Substance RBF-H |  |  |  | 7 |  |  | 7 | 7 |  |  |
| Antitumor activity (inhibiting ratio (%)) |  | 0 | 0 | 0 | 0 | 0 | 13 | 43 | 95 | 93 | 91 |

Note:
Five mice were included in each test group.

EXAMPLE 9

(Solid Tumor Inhibiting Test)

Cells of ascites type sarcoma 180 cultivated in the peritoneal cavity of ICR mice for 7 days were transplanted, in numbers of $5 \times 10^6$ cells per mouse, into the muscles of the right hind legs of ICR mice, female, 5 weeks age. Five mice were included in each test group. After 24 hours had passed, an aqueous saline solution containing the sample to be tested was administered into the peritoneal cavity once a day, for 10 days. The tumors in the mice were taken out on the end of 4 weeks and weighed for comparison with the results obtained by the control sample. The tumor-inhibiting ratio was calculated according to the equation described below.

$$\text{Inhibiting Ratio (\%)} = \left(1 - \frac{\text{Tumor Volume (Sample)}}{\text{Tumor Volume (Control)}}\right) \times 100$$

The results are set forth below:

|  | Dosage (mg/kg · day) | Inhibiting Ratio (%) |
|---|---|---|
| RBF-P obtained in Example 4 | 10 | 32 |
| RBF-X obtained in Example 4 | 200 | 43 |
| RBF-H obtained in Example 4 | 20 | 44 |

EXAMPLE 10

The same procedures as described in Example 4 were repeated with the exceptions that a rice bran identical to that of Example 1 was used, and that 5% aqueous sodium hydroxide solution was used in place of the 4% aqueous sodium hydroxide, and that the period and temperature for the extraction were varied, to obtain the substance RBF-P. The yields and activities of the thus-obtained substances RBF-P are set forth below, in which the activity was determined by the same TPCV method as described in Example 2 and expressed by the symbols (+++) for 90% or more (preventing ratio), (++) for 60–89%, (+) for 35–59% and (−) for 34% or less, based on the dosage of 100.

| Temperature (°C.) | Period (hours) | Yield (g/kg of rice bran) | Activity |
|---|---|---|---|
| 30 | 40 | 32 | ++ |
| 30 | 110 | 31 | +++ |
| 12 | 40 | 27 | − |
| 12 | 110 | 38 | ++ |
| 50 | 5 | 52 | + |
| 50 | 10 | 46 | +++ |
| 50 | 20 | 24 | +++ |
| 50 | 30 | 0.4 | − |
| 50 | 40 | 0.4 | − |
| 80 | * | 54 | + |
| 80 | 5 | 4 | + |

Note:
* = cooled just after the temperature reached 80° C.

EXAMPLE 11

To 5% aqueous sodium hydroxide solution extract of the rice bran obtained in the same method as in Example 1, was added water in the same amount as that of the extract. The resultant was then mixed with various amounts of methanol or acetone to produce aqueous organic solvent solutions concentrations of which ranged from 40 to 80%. The insoluble of the basic solution was removed and the solution was adjusterred to have pH 5.5 by addition of hydrochloric acid. The so produced acidic solution was allowed to stand overnight at a temperature of lower than 10° C. and the precipitate was collected. The precipitate was then dried by the freeze-drying procedure to give RBF-P.

The following Table 4 shows concentrations of organic solvents (volume %), yield of RBF-P (g/kg rice bran) and the TPCV activity (dosage 100 mg/kg).

TABLE 4

| solvent | concentration | Yield of RBF-P | TPCV | activity |
|---|---|---|---|---|
| methanol | 40 | 51 | − | − |
|  | 60 | 68 | + | + |
|  | 80 | 99 | + | + |
| acetone | 30 | 57 | − |  |
|  | 50 | 41 | + | ++ |
|  | 70 | 0 |  |  |

EXAMPLE 12

RBF-P was obtained in the same manner as in Example 11, except for using ethanol instead of methanol and acetone to give 50 volume % ethanol aqueous solution and adjusting pH volume to 5.5 by using hydrochloric acid, sulfuric acid or phosphoric acid. Both of the yield of RBF-P and the activity were good.

| acids used | Yield of RBF-P | TPCV | activity |
|---|---|---|---|
| hydrochloric acid | 95 | ++ | (87%) |
| sulfuric acid | 114 | ++ | (89%) |
| phosphoric acid | 90 | +++ | (92%) |

EXAMPLE 13

To 100 g of rice bran obtained from the rice grain belonging to species Sasanishiki and Koshihikari was added 1.4 liters of water and the mixture was heated under a normal pressure for 5 hrs. to dissolve the portion soluble in hot water. The resulting mixture was filtered while heated, to collect 135 g of the solid portion. The so obtained solid portion was mixed with 250 g of 5% aqueous sodium hydroxide solution and then was allowed to stand at 50° C. for 10 hrs. to extract a portion soluble in an aqueous basic solution.

To 100 g of the extract was added 100 g of water, and to the aqueous mixture was further added 200 ml of ethanol so that an ethanol concentration was adjusted to 50%. The alkaline ethanol-insoluble was removed by a centrifuge. The filtrate was adjusted to pH 5.5 with HCl and allowed to stand overnight at 4° C. The precipitate thus produced was collected and dried to give 2.47 g of the substance RBF-P in the form of a dry precipitate (95 g/1 kg rice bran)

The embodiments of the invention in which an exclusive property or privilege is claimed are defined as follows:

1. A protein substance, called RBF-PM, having an amino acid composition consisting essentially of:

|  | % by weight |
| --- | --- |
| aspartic acid | 8–12 |
| threonine | 1–5 |
| serine | 1–5 |
| glutamic acid | 11–16 |
| proline | 1–5 |
| glycine | 4–8 |
| alanine | 5–9 |
| cystine | less than 0.1 |
| valine | 7–12 |
| methionine | 1–3 |
| leucine | 8–16 |
| isoleucine | 4–8 |
| tyrosine | 2–5 |
| phenylalanine | 5–9 |
| lysine | 3–6 |
| histidine | 1–5 |
| arginine | 4–9 | said substance having an elemental analysis as follows:

|  | % by weight |
| --- | --- |
| carbon | 47–54 |
| hydrogen | 6–8 |
| nitrogen | 12–15 | said substance containing from 0 to 8% by weight of saccharide, determined by the phenol-sulfuric acid method, said substance having an infrared spectrum as shown in FIG. 2 of the attached drawings, said substance having molecular weights mainly distributed in both of the ranges of 30,000–50,000 and 70,000–120,000, said substance having an isoelectric point in the range of pH3 to pH6, said substance being insoluble in dilute aqueous sodium chloride solution and dilute aqueous acid and being soluble in dilute aqueous alkaline solution.

2. A protein substance called RBF-PM, as claimed in claim 1 which is insoluble or sparingly soluble in pure water, 0.85% aqueous sodium chloride solution, methanol, ethanol (100%, 70%), acetone, methyl ethyl ketone, ethyl ether, isopropyl ether, ethyl acetate, butyl acetate, 7-M aqueous urea solution, phosphoric acid buffer (pH 4.7–7), citric acid buffer (pH 3.3–7), acetic acid buffer (pH 3.7–8), hydrochloric acid (0.1N, 6N), and 0.1-M aqueous acetic acid; partly soluble in 3-M guanidine hydrochloride solution, and soluble in 6-M guanidine hydrochloride solution, aqueous sodium hydroxide solution (0.0125N), aqueous alkaline alcoholic solution (0.0125N, 50% in volume), aqueous sodium laurylsulfate solution (0.1%), aqueous sodium dodecylbenzenesulfonate solution (0.1%), and glacial acetic acid.

3. A protein substance, called RBF-PM, as claimed in claim 1 which is obtained by the process comprising the steps of:

extracting, at a temperature of from 10° to 90° C., a hot water-insoluble portion of rice bran with an extracting liquid consisting essentially of an aqueous alkaline solution of a base selected from the group consisting of sodium hydroxide, sodium carbonate, potassium hydroxide and ammonia, at a temperature of from 10° to 90° C., to obtain an aqueous alkaline extract of said portion of rice bran;

mixing said aqueous alkaline extract with an organic, water-miscible solvent selected from the group consisting of ethanol, methanol, n-propanol, isopropyl alcohol and acetone, to form an aqueous alkaline organic solvent solution and to precipitate a first material which is insoluble in said aqueous alkaline organic solvent solution;

removing said first material from said aqueous alkaline organic solvent solution;

then adding an acid selected from the group consisting of hydrochloric acid, phosphoric acid, sulfuric acid and acetic acid, to said aqueous alkaline organic solvent solution until the pH of said aqueous organic solvent solution is from 3 to 7 and thereby precipitating a second material;

recovering said second material;

then mixing said second material with methanol and thereby dissolving the methanol-soluble fraction of said second material; and then recovering the methanol-insoluble fraction of said second material, which methanol-insoluble fraction is said protein substance RBF-PM.

4. A protein substance, called RBF-PM, as claimed in claim 3, wherein said rice bran is Japonica or Indica rice bran.

5. A protein substance, called RBF-PM, as claimed in claim 3, wherein said rice bran comprises bran of at least one rice species selected from the group consisting of *Shonai sasanishiki, Iwate kiyonishiki, Fushikima sasanishiki, Saitama nihonbare* and mixtures thereof.

6. A protein substance, called RBF-PM, as claimed in claim 3, wherein said rice bran is obtained from a mixture of *Shonai sasanishiki, Iwate kiyonishiki* and *Saitama nihonbare*, said substance has an amino acid composition consisting essentially of:

Aspartic acid—9.2
Threonine—3.0
Serine—2.5
Glutamic acid—13.2
Proline—4.0
Glycine—5.9
Alanine—6.9
Cystine—0
Valine—10.4
Methionine—1.1

Leucine—14.4
Isoleucine—5.7
Tyrosine—3.3
Phenylalanine—6.7
Lysine—4.8
Histidine—2.8
Arginine—6.3 and said substance has an elemental analysis of:
carbon—51.19
hydrogen—7.04
nitrogen—12.31.

7. A protein substance, called RBF-PM, as claimed in claim 3, wherein said rice bran is obtained from a mixture of grains of koshihikari rice, said substance has an amino acid composition consisting essentially of:
Aspartic acid—9.5
Threonine—4.3
Serine—4.6
Glutamic acid—14.6
Proline—1.6
Glycine—5.5
Alanine—6.8
Cystine—0
Valine—8.0
Methionine—2.3
Leucine—8.7
Isoleucine—7.6
Tyrosine—4.6
Phenylalanine—6.5
Lysine—4.7
Histidine—2.8
Arginine—7.9 and said substance has an elemental analysis of:
carbon—48.89
hydrogen—6.91
nitrogen—13.56.

8. A substance, called RBF-H, which is obtained by the process comprising the steps of:
extracting, at a temperature of from 10° to 90° C., a hot water-insoluble portion of rice bran with an extracting liquid consisting essentially of an aqueous alkaline solution of a base selected from the group consisting of sodium hydroxide, sodium carbonate, potassium hydroxide and ammonia, to obtain an aqueous alkaline extract of said portion of rice bran;
mixing said aqueous alkaline extract with an organic, water-miscible solvent selected from the group consisting of ethanol, methanol, n-propanol, isopropyl alcohol and acetone, to form an aqueous alkaline organic solvent solution, and to precipitate a first insoluble material which is insoluble in said aqueous alkaline organic solvent solution;
removing said first insoluble material from said aqueous alkaline organic solvent solution;
adding an acid selected from the group consisting of hydrochloric acid, phosphoric acid, sulfuric acid and acetic acid, to said aqueous alkaline organic solvent solution until the pH of said aqueous organic solvent solution is from 3 to 7 and thereby precipitating a second insoluble material;
recovering said second insoluble material;
then mixing said second insoluble material with a polar organic solvent selected from the group consisting of methanol, ethanol, n-propanol, isopropanol, butanol, acetone, methyl ethyl ketone, cyclohexanone, ethyl acetate, butyl acetate, diethyl ether, diisopropyl ether and tetrahydrofuran, and thereby dissolving a soluble fraction of said second insoluble material which is soluble in said polar organic solvent;
then recovering said soluble fraction;
then mixing said soluble fraction with hexane to precipitate a third insoluble material; and
recovering said third insoluble material as said substance RBF-H, said substance RBF-H having an infrared spectrum as shown in FIG. 5 of the attached drawings, said substance having an elemental analysis of C, 52.43% by weight; H, 7.79% by weight; N, 6.67% by weight; ash, 4.36% by weight.

9. A composition consisting essentially of a mixture of the substance RBF-H as claimed in claim 8 and a higher fatty acid.

10. A composition as claimed in claim 9, in which said higher fatty acid is selected from the group consisting of oleic acid, linoleic acid, palmitic acid and mixture thereof.

11. A substance, called RBF-H, as claimed in claim 8, wherein said rice bran is Japonica or Indica rice bran.

12. A substance, called RBF-H, as claimed in claim 8, wherein said rice bran comprises bran of at least one member selected from the group consisting of *Shonai sasanishiki, Iwate kiyonishiki, Fushikima sasanishiki, Saitama nihonbare* and mixtures thereof.

13. A process for preparing a substance, called RBF-P, consisting essentially of the steps of:
extracting, at a temperature of from 10° to 90° C., a hot water-insoluble portion of rice bran with an extracting liquid consisting essentially of an aqueous alkaline solution of a base selected from the group consisting of sodium hydroxide, sodium carbonate, potassium hydroxide and ammonia, to obtain an aqueous alkaline extract of said portion of rice bran;
mixing said aqueous alkaline extract with an organic, water-miscible solvent selected from the group consisting of ethanol, methanol, n-propanol, isopropyl alcohol and acetone, to form an aqueous alkaline organic solvent solution and to thereby precipitate material which is insoluble in said aqueous alkaline organic solvent solution;
removing said insoluble material from said aqueous alkaline organic solvent solution;
then adding an acid selected from the group consisting of hydrochloric acid, phosphoric acid, sulfuric acid and acetic acid, to said aqueous alkaline organic solvent solution until the pH of said aqueous organic solvent solution is from 3 to 7 and thereby precipitating said substance; and
then recovering said substance RBF-P.

14. A process as claimed in claim 13, in which the concentration of said organic solvent is not less than 40% by volume, based on the mixture of the aqueous extract solution and said organic solvent.

15. A process as claimed in claim 14, in which said organic solvent is ethanol.

16. A process for preparing a substance, called RBF-X, which consists essentially of the steps of:
treatment the substance RBF-P obtained by the process of claim 13 with a polar organic solvent selected from the group consisting of methanol, ethanol, n-propanol, isopropanol, butanol, acetone, methyl ethyl ketone, cyclohexanone, ethyl acetate, butyl acetate, diethyl ether, diisopropyl ether and tetrahydrofuran, to obtain a solution; and removing said polar organic solvent from the solution by evaporation to thereby obtain said substance RBF-X.

17. A process for preparing a substance, called RBF-PM, which consists essentially of the steps of:
    treating the substance RBF-P obtained by the process of claim 13 which a polar organic solvent selected from the group consisting of methanol, ethanol, n-propanol, isopropanol, butanol, acetone, methyl ethyl ketone, cyclohexanone, ethyl acetate, butyl acetate, diethyl ether, diisopropyl ether and tetrahydrofuran, to obtain a solution and insolubles; and
    separating the insolubles from the solution, which insolubles comprise said substance RBF-PM.

18. A process as claimed in claim 13, wherein said rice bran is Japonica or Indica rice bran.

19. A process as claimed in claim 13, wherein said rice bran comprises bran of at least one member selected from the group consisting of Shonai sasanishiki, Iwate kiyonishiki, Fushikima sasanishiki, Saitama nihonbare and mixtures thereof.

20. A process for preparing a substance, called RBF-H, which consists essentially of the steps of:
    treating the substance RBF-X obtained by the process of claim 16 with hexane to precipitate an insoluble material; and
    recovering said insoluble material as said substance RBF-H.

21. A process as claimed in claim 15 in which the ethanol content of said aqueous alkaline organic solvent solution is from 40 to 60% by volume.

22. A process as claimed in claim 13 in which said organic solvent is methanol and the amount of methanol in said aqueous alkaline organic solvent solution is from 4 to 5 times the volume of said aqueous alkaline extract.

23. A process as claimed in claim 13 in which said pH is from 4 to 6.

* * * * *